United States Patent [19]

Kater

[11] Patent Number: 4,461,998

[45] Date of Patent: Jul. 24, 1984

[54] ION SELECTIVE MEASUREMENTS

[76] Inventor: John A. R. Kater, 2037 W. San Lorenzo, Santa Ana, Calif. 92704

[21] Appl. No.: 307,750

[22] Filed: Oct. 2, 1981

[51] Int. Cl.³ ............................................. G01N 27/56
[52] U.S. Cl. .................................... 324/438; 204/1 T; 204/412; 204/416; 204/433; 324/425
[58] Field of Search ................ 324/438, 425; 204/1 T, 204/412, 416, 433, 435; 422/101, 102, 68; 436/150, 163, 178

[56] References Cited
U.S. PATENT DOCUMENTS 2,288,180   6/1942   Brengman et al. ................ 324/438

Primary Examiner—Michael J. Tokar
Assistant Examiner—Kevin D. O'Shea
Attorney, Agent, or Firm—Grover A. Frater

[57] ABSTRACT

A reference electrode (102), standard calibration solutions (72 and 76) and a sample solution (80) are all placed in liquid contact with one another and a reference solution (70). Contact between the reference solution (70), the sample (80) and the calibration solutions (72 and 76) is made through salt bridges (82, 74 and 78). A special conical shaped solution container (FIG. 5) having a porous plug or other salt bridge extending through the container wall at the apex provides special advantage.

23 Claims, 6 Drawing Figures

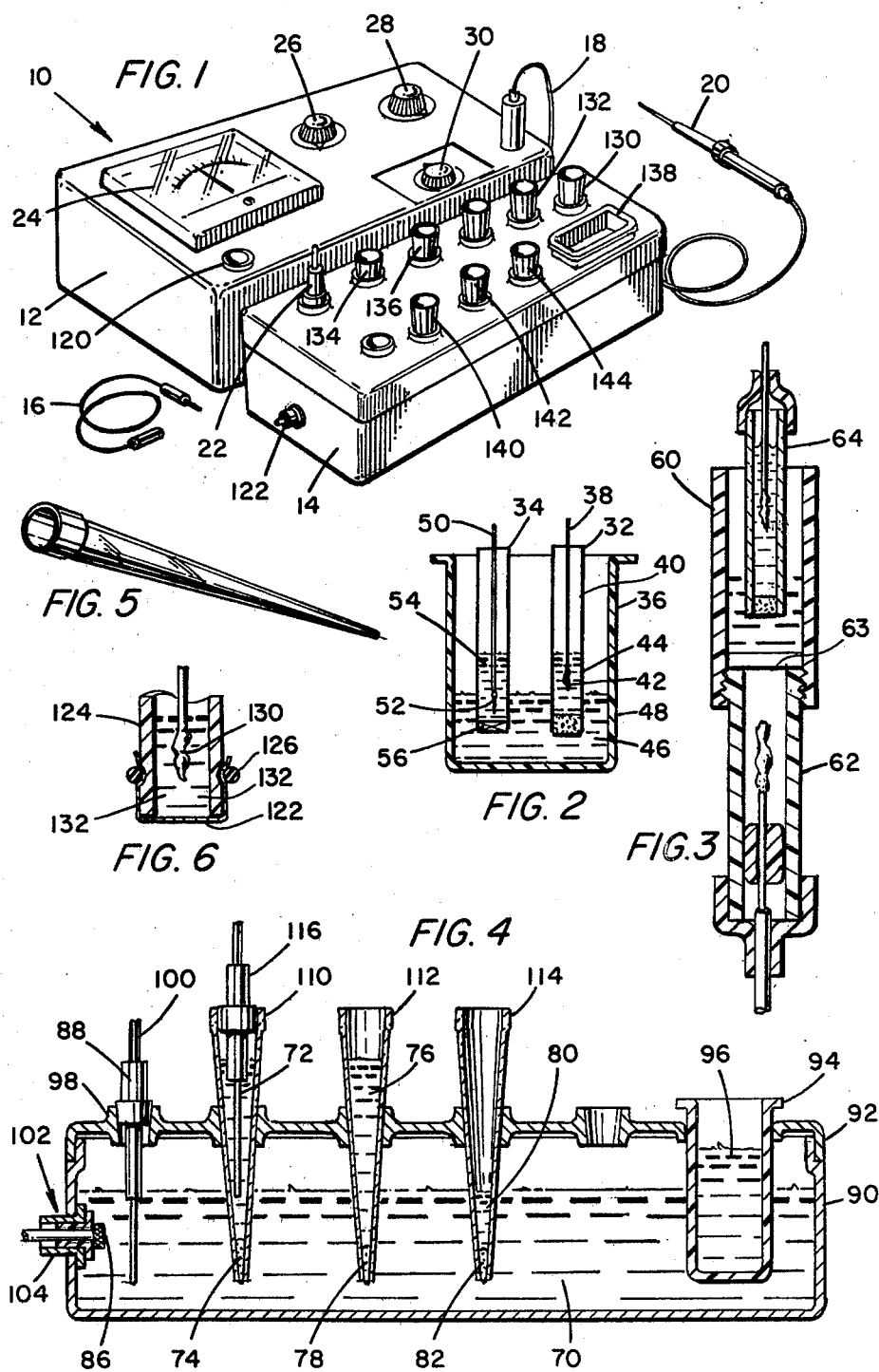

ION SELECTIVE MEASUREMENTS

TECHNICAL FIELD

This invention provides improved apparatus and improved methods for measuring ion concentration.

BACKGROUND ART

Concentrations of sodium, potassium, calcium, chloride and materials in solutions and the determination of pH can be made electrically with electrodes that are selective to ions of those materials. The standard reference text in this field is *Reference Electrodes Theory and Practice* by Ives and Janz. That work and the patent literature make it clear that measurement is difficult. The potentials are minute, they vary with temperature, the measuring circuit necessarily includes junctions between dissimilar materials and metal to liquid junctions across which interfering potentials appear at magnitudes comparable to the potentials to be measured.

Practical measurement has been characterized by short term drift in potentials and need for frequent calibration, often in reference solutions which differ in large degree from the composition of the test solution, and that results in error and uncertainty about accuracy of measurements. Attempts to overcome these difficulties have concentrated on design of voltmeters, on finding new or improved ion selective "membrane" materials, and on design of the electrode structure primarily in an effort to avoid "poisoning" and fouling of electrodes and to minimize the effect of interfering ions by the sample being measured. The price for improvement is usually higher cost, but the advantage of such improvements is often lost in the need to extend the use of the more expensive electrode over longer periods or a greater number of tests.

The prior art is illustrated in FIGS. 2 and 3 of the drawing. The two electrodes, one the reference electrode and the other the ion selective electrode, are placed in a first body of electrolyte called a standard solution, and the voltmeter is calibrated. Then the electrolyte is removed and is replaced with a second body of standard solution and the slope of the voltmeter reading change is adjusted. Thereafter, the second body of electrolyte is removed and replaced with the sample to be tested. In that process each measurement is a separate event in which the measuring circuit is reconstructed both on the reference side and on the ion selective side. Temperatures of the solutions and the sample may vary, and a relatively large amount of sample is required. The measurement steps are usually separated by rinsing steps in which there is opportunity to alter junction potential equilibria at the electrodes.

Special electrodes and techniques have been developed in an effort to speed the measurement process and improve accuracy. FIG. 3 shows one of the more advanced of those developments. The ion selective electrode is inverted and inserted in the lower end of a tube. The ion selective membrance forms the bottom wall of a sample cup into which the reference electrode is lowered as the cup is filled successively with mid-range reference solution, rinse material, end-range reference solution, rinse material, and sample solution. This structural arrangement has some advantages, but the major causes of error and uncertainty remain. The circuit is interrupted both on the reference electrode side and on the ion selective side, and there is opportunity for error caused by liquid-junction-potential variations at both the measuring and reference electrode.

DISCLOSURE OF INVENTION

The invention alters the basic geometry of the measuring structure to provide a unified structural and liquid form. Temperatures are, or can be, common. Less circuit and liquid junction interruption is necessary, smaller samples can be measured and accuracy equal to or better than that of the best prior art systems is achieved in a simple, fast test procedure.

The invention provides an apparatus and a procedure in which a single body of reference electrolyte solution is electrically and thermally connected to the standard calibration solutions, to the sample solution, and to the reference electrode. In the preferred embodiment, a quantity of the reference electrolyte is used for rinsing, and it is in thermal contact with the body of reference solution.

Several very special advantages arise from the use of a common pool of reference electrolyte and from a method in which only the ion sensitive electrode is moved. The saturated salt solution that characterizes reference electrodes is not needed. An ion sensitive electrode, "ISE," can be substituted for the conventional metal/metal salt/saturated salt solution/porous plug reference electrode. The conventional metal/metal salt/saturated salt solution/porous plug reference electrode can now be substituted by just another half cell such as a silver/silver chloride wire or by another ISE. The use of another ISE allows measurements in the differential mode. Moreover, the reference ISE need not be selective to the same ion as the indicating ISE. The reference electrolyte and the center scale standard solution, or the end of scale standard solution, may be the same material. When measuring for two ions, each ISE can serve as the reference electrode for the other.

These features and advantages, and others, including a special conical sample container, that will be apparent upon an examination of the description of preferred embodiments that follows are more readily understood when considered in connection with the accompanying drawing. It is to be understood that the embodiment shown has been selected for illustration as the best mode for practicing the invention. Other embodiments are possible and in particular applications a different embodiment may prove to be preferable. It is also to be understood that the range of equivalent structures and steps in the invention is not limited to those mentioned herein by name.

BRIEF DESCRIPTION OF THE DRAWING

In the drawing:

FIG. 1 is an isometric drawing of an apparatus which embodies the invention and may be used in measuring and determining the presence of ions according to the method of the invention;

FIG. 2 is a diagramatic showing of prior art apparatus used in the explanation of the prior art structure and its use;

FIG. 3 is a cross-sectional view taken on a plane through its vertical centerline of an advanced form of prior art apparatus;

FIG. 4 is a diagram intended to serve as a generalized showing of the structure of the invention;

FIG. 5 is an isometric view of the conical container which is the preferred form of small sample container; and FIG. 6 is a cross-sectional view of one end of an electrode employing a hydrophillic membrane.

DESCRIPTION OF THE PREFERRED EMBODIMENT

In FIG. 1 the ionic potential measuring set 10 includes a millivoltmeter 12, a solution tray 14, a reference electrode connector cable 16, an ion selective electrode connector cable 18, an ion selective electrode 20 which is plugged into cable 18, and another ion selective electrode 22 which is mounted in the solution tray 14.

The millivoltmeter includes an analog meter 24, a calibration dial 26, a slope setting dial 28, and a mode selection switch 30. The meter shown will make measurements of "absolute" voltage, or differential voltage, and has selectable internal circuitry for measuring any of pH or $Ca^{++}$, $Na^+$, $K^+$ and $Cl^-$ ions. The meter face is marked with a separate scale for each of these variables. The electrodes provide signals which are sufficiently accurate and reliable so that expensive meters are not required. Some users may prefer to replace the meter with multiple ion measurement capability with separate millivoltmeters each having a single scale meter face to insure against confusion.

Whether it be the form shown or a single scale meter, the meter 12 can be used to practice either the prior art measurement method or the method of the invention.

The prior art method was practiced with apparatus represented by FIG. 2. In FIG. 2 a reference electrode 32 and an ion selective electrode 34 are mounted together in a container 36. Silver wire 38 extends into the body of reference electrode 40. The end of the wire is coated with silver chloride 42 and, with the silver chloride, is immersed in a saturated solution 44 of potassium chloride. That solution is in liquid communication with a body of solution 46 in container 36. A plug of porous material extends through the wall of the electrode body. Solution 44 migrates downwardly and solution 46 migrates upwardly through the plug until the solutions join to form a liquid path for migration of ions between the bodies of solutions. The result is called a "salt bridge" 48.

Continuing in FIG. 2, silver wire 50 extends into the body of ion selective electrode 34 where its silver chloride covered end 52 is immersed in an electrolyte 54 which, in this case, is a quantity of salt solution also containing the ion sought. The ion to which the electrode is selective develops a potential at the ion selective "membrane" 56 according to the mechanism of selectivity for that ion.

If the selective electrode is selective to pH the two silver wires 38 and 50 would be connected across a meter like meter 12, and, as a first step, the meter would be calibrated. The mid-value in the range of pH values is 7. Solution 46 would be a standard reference solution having pH 7. In that case the meter pointer should point to 7 on the meter's pH scale. To calibrate the meter the operator rotates the calibration knob 26 until the meter current that flows in response to the potential across wires 38 and 50 moves the pointer over 7 on the scale.

That having been done, the operator removes the pH 7 solution from the container 36, rinses the container and then adds another quantity of standard reference solution the pH of which is higher or lower than 7 and has a value nearly that of one end of the range of expected pH values. Thus, it might have a pH of 4. The salt bridge 48 and ion selective membrane 56 being immersed in pH 4 solution, the operator adjusts the slope dial 28 until the meter pointer overlies pH 4 on the meter scale. Then the pH 4 solution is removed from container 36, the container is rinsed and the sample whose PH is to be measured is added to the container.

If the temperature of the two standard solutions and the sample are the same, if the saturation of the salt bridge was complete at the beginning of calibration, and if the test is completed before calibration drifts, the meter pointer will overlie the pH value that characterizes the sample.

The potassium concentration range in blood extends from a low of 2 milli molar/L to a high of 8 milli molar/l. The mid value is 4. In the case of potassium, the mid range standard solution produces a deflection of 4 on the properly calibrated meter scale. The high end standard solution produces a deflection of 8 on the scale when the slope adjustment is proper.

While the method thus described has been standard in the prior art, it may be modified in particular applications. One important modification is practiced with electrodes arranged as they are in FIG. 3. When making measurements on blood, the quantity of sample may be limited. In FIG. 3 the sample container 60 is fixed at the end of an inverted ion selective electrode 62. The ion selective membrane 63 forms the bottom wall of the sample container.

The container is filled with the mid range standard solution, the meter is calibrated, the standard solution is aspirated from the container and replaced with rinse fluid. The rinse fluid is aspirated out and the container is filled with range end standard solution. After slope adjustment, that solution is aspirated out and replaced with rinse fluid which is aspirated out and replaced with the test solution. The procedure is as complex, or even more complex, than the previously described procedure. The reference electrode 64 need be no different than electrode 38, but the ion selective electrode 62 is special in that its design must preclude bubble formation in its electrolyte chamber for inverted operation. The only advantage in this improvement is that the sample quantity may be less.

The prior art method is characterized by a succession of solution changes. The several solutions are isolated one from the others. Each step is independent of the others except that the results of the preparatory steps are stored in the position of the adjustable elements of the meter. In the invention the solutions are linked electrically and thermally throughout the measurement process. The whole set of interface potentials is developed and maintained simultaneously, and the only change lies in movement of the ion selective electrode from one to the other of the solutions.

FIG. 4 illustrates schematically how the invention is practiced. The large body of reference solution is numbered 70. The body of standard mid-range calibrating solution 72 is in liquid contact with the reference solution 70 in a "salt bridge" 74. Another body 76 of fluid, a standard range-end calibrating solution, is in liquid contact with reference solution 70 in a salt bridge 78, and a body of sample solution 80 is in liquid contact with reference solution 70 in a salt bridge 82. There are two reference electrodes, both immersed in reference solution 70. One reference electrode is no more than a metal button 86 which has a salt of that metal bonded to the button surface. The other reference electrode 88 is an ion selective electrode the ion selective element of which is immersed in the reference solution.

The reference solution 70 is contained in container 90. The container may have a variety of shapes. In this case it is molded of plastic and its exterior surface is metalized to render it electrically conductive. Conductivity provides shielding against external fields.

The cover 92 is plastic and its outer surface and lower rim are metalized to complete the shielding against external fields. The cover is formed with apertures which are shaped to receive and hold containers for the two calibrating solutions and one or more sample solutions. Another aperture receives a container 94 for a body 96 of rinsing solution.

A nipple 98 extends upwardly from the cover and is sized to hold the shank of the miniature reference electrode 88 with the active, ion selective membrane of the electrode in the reference solution 70. Connector plug 100 of the electrode is exposed for connection to a cable jack. The reference electrode 102, which comprises silver button 84 and silver chloride overlay 86, also comprises a connector plug 104 exposed at the exterior of the container 90 where it can be connected to the cable jack.

The two standard solutions 72 and 76, and the sample 80 are contained in three conically shaped containers 110 112 and 114, respectively. The preferred form is shaped like a disposable pipette tip as best illustrated in FIG. 5. The representation in FIG. 4 is schematic. A porous plug is lodged in the apex opening of each conical container. Upon being wetted these plugs serve as salt bridges. Wood is a suitable material. Plugs 74, 78 and 82 are formed of wood shaped not unlike the tip ends of round toothpicks. Arranged as they are, the plugs are soon wetted completely through and are completely operable. Another suitable material is a hydrophillic dialysis (cellulose acetate) membrane stretched over the opening like a drumhead. So, too, in the case of the ion selective electrode 116 which is inserted in the container 110 and the standard solution 72 which it contains. Some ion selective membranes require soaking. In FIG. 4, both of the electrodes 88 and 116 are soaking and, by the provision of more apperatures, more could be set to soak.

The apparatus of FIG. 4 is ready for use. The electrodes and salt bridges are fully operative. The electrical interface between the several solutions is established and stabilized. Temperature stability has been established. It remains only to connect the reference and ion selective electrode terminals to the voltmeter and to adjust the calibration dial until the meter reading corresponds to the value of the standard fluid 72. That having been done, the electrode 116 is removed from container 110 and is rinsed in rinse fluid 96. Then the electrode is placed in the standard solution in container 112. The slope dial is adjusted until the meter dial corresponds to the value of solution 76 after which the electrode is rinsed in rinse fluid 96. Next, the electrode is placed in the sample 80 in container 114. The meter reading corresponds to the ion content of the sample.

When measuring in the normal mode, the reference electrode 102, or a conventional reference electrode, is used. When measuring in the differential mode, one or the other of the ion selective electrodes 88 and 116 may be used as the reference, and the other as the measuring electrode. The standard calibration solutions contain the ion to be detected.

It is possible to make the measurement if the two reference electrodes are selective to different ions. It is also possible to use two ion selective electrodes each sensitive to a different ion and each serving as the reference electrode while measuring with the other. Two sets of standard calibration solutions are required in that case.

The tray 14 in FIG. 1 is set up to make potassium and calcium measurements. Electrode 20 is selective to potassium ions, and electrode 22 is selective to calcium ions. A quantity of standard potassium calibration solution is contained in each of conical containers 130 and 132. They contain mid-range and high range concentrations, respectively. Container 134 contains midrange standard calcium concentration, and container 136 contains the high range standard calcium concentration. Rinse solution is contained in container 138. Conical containers 140, 142 and 144 each contain a sample to be analyzed. The cable 16 connects jack 120 on the meter and the reference electrode jack 122 on the tray. Switch 30 is turned to measurement in the standard mode—first for one of potassium or calcium. When the measurement is completed, switch 30 is rotated to the measuring position for the other.

The set shown is intended for use in operating rooms and in nurseries to measure blood chemistry. As little as ten microliters of sample is required in the tapered sample container, so the set is even useful for measuring blood samples taken from neonates. The volumetric ratio of sample to the pool of reference solution is in the order of 1 to 30,000, so temperature equilibrium is reached rapidly.

The invention is useful in a wide variety of special applications because of its portability and because of its versatility. Both standard and differential mode measurement is available, maintenance is simple, the conical containers can be made inexpensively and are normally thrown away after use. There is no need to risk fouling or plugging of salt bridges. Electrolytes can be changed without changing electrode components. Moreover, a wide range of solutions can be used as the reference solution pool. The reference material can be any conventional electrolyte such as 3M KCl. It can be the same as any of the standard calibrating solutions. or the sample. It can even be blood or blood serum or reconstituted serum.

Making measurements in the differential mode is particularly useful when the sample contains an interfering measurement. To overcome that difficulty, some lithium is added to the standard calibration solution and the solution is then used both as the standard solution and the reference solution. Then measurement in the differential mode results in cancellation of the interfering effect.

The reference electrode 120 of FIG. 6 uses a hydrophillic membrane as its "salt bridge" material. The purpose of the salt bridge in reference electrodes is to provide a path for ionic migration between test solution and the reference half cell. If the porosity of the salt bridge material is high, salt from inside the cell can pass through the bridge and contaminate the sample. Also, proteins and blood plateletts can plug the pores of the bridge material and generate a residual junction potential. Using the hydrophillic membrane eliminates actual liquid flow but does allow ion passage. Contamination of the hydrophillic material is minimal. The preferred material is cellulose acetate, and it forms the membrane 122 of FIG. 6. The membrane covers the end of the tube 124 and extends up along the sides of the tube where it is held in place by an O-ring 126. The tube houses the usual half cell 130 electrode and electrolyte 132.

Although I have shown and described certain specific embodiments of my invention, I am fully aware that many modifications thereof are possible. My invention, therefore, is not to be restricted except insofar as is necessitated by the prior art.

I claim:

1. Apparatus for use in measuring for the presence of selected ions comprising:
    electrolyte container arranged to contain a body of electrolyte;
    a reference electrode;
    an ion selective electrode including an ion selective element;
    a standard solution container;
    a sample solution container;
    each of said standard solution container and said sample solution container including an ionic bridge element extending through its wall; and
    holding means for holding said ion selective element and said reference electrode and the bridge elements in said electrolyte container such as to be immersed in the body of electrolyte when contained in said electrolyte container.

2. The invention defined in claim 1 in which said reference electrode comprises a metal and a salt of that metal.

3. The invention defined in claim 2 in which said reference electrode further comprises an electrolyte in which said metal and metal salt are disposed in an ion selective element interposed to separate said metal and metal salt and electrolyte from any body of electrolyte in said electrolyte container.

4. The invention defined in claim 1 in which said reference electrode comprises a second ion selective electrode.

5. The invention defined in claim 1 which further comprises a second standard solution container including a bridge element extending through its wall;
    said holding means being effective to hold the bridge element of said second standard solution container such as to be immersed in the body of electrolyte when contained in said electrolyte container.

6. The invention defined in claim 1 which further comprises a rinse solution container and means for holding said rinse solution container in thermal contact with the body of electrolyte when contained in said electrolyte container.

7. The invention defined in claim 1 which further comprises means for measuring the potential between said reference electrode and said ion selective electrode whether the ion selective electrode be inserted in said standard solution container or in said sample container.

8. The invention defined in any of claims 1, 2, 4, 6 or 7 which further comprises a body of electrolyte contained in said electrolyte container and in which said reference electrode and said bridge elements of said standard solution container and said sample solution container are in intimate contact.

9. The invention defined in claim 1 in which said sample container is elongated and conical, the bridge element extending through the wall of the cone in the region of its apex.

10. The invention defined in claim 9 in which said ion selective electrode is shaped such that its ion selective element is positioned proximate to said bridge element of the sample container when the ion selective electrode is inserted into said sample container.

11. In combination:
    an ion selective electrode having an ion selective element;
    a reference electrode;
    a first standard solution container having a salt bridge extending through its wall;
    a sample solution container having a salt bridge extending through its wall; and
    holding means for holding said ion selective element and said reference electrode and said salt bridges in intimate contact with a body of electrolyte.

12. The invention defined in claim 11 which further comprises a body of standard solution contained within said first standard solution container.

13. The invention defined in claim 11 which further comprises a body of electrolyte and a rinse liquid container said holding means being effective to hold said ion selective element and said reference electrode and said salt bridges in intimate liquid and thermal contact with said body of electrolyte and to hold said rinse liquid container in thermal contact with said body of electrolyte.

14. The invention defined in claim 13 which further comprises a second standard solution container having a salt bridge extending through its wall;
    a first body of standard solution in the standard solution container first mentioned; and
    a second body of a different standard solution in said second standard solution container.

15. The invention defined in claim 14 in which said first and second standard solution containers and said sample solution containers are conical, their respective salt bridges being formed in the regions of their apexes.

16. The method of conducting tests to determine ion content in a sample fluid using a voltmeter connected between a reference electrode and an ion selective electrode, which method comprises the steps of:
    immersing the reference electrode in a body of electrolyte;
    placing a standard calibrating solution and a sample solution in intimate liquid contact with one another and with said reference electrode in said electrolyte through a salt bridge;
    placing the ion selective electrode in the standard calibrating solution and calibrating the voltmeter; and
    placing the ion selective electrode in the sample solution.

17. The method defined in claim 16 which comprises the further step of rinsing the ion selective electrode in a quantity of said electrolyte after placement in said standard calibration solution and before placement in said sample solution.

18. The method defined in claim 16 in which said reference electrode comprises the combination of a metal and a salt of that metal.

19. The method defined in claim 16 in which said reference electrode comprises a second ion selective electrode.

20. The method defined in claim 16 which comprises the further step of adding quantities of an interfering ion to said electrolyte and to said standard calibration to equal concentration.

21. The method defined in claim 20 in which the electrolyte is a quantity of the standard calibration solution.

22. The invention defined in claim 1 in which said reference electrode includes a bridge element formed of a hydrophillic membrane material.

23. The invention defined in claim 1 in which said reference electrode includes a bridge element formed of cellulose acetate.

* * * * *